(12) United States Patent
Olson

(10) Patent No.: US 10,159,802 B2
(45) Date of Patent: Dec. 25, 2018

(54) MEDICAMENT DELIVERY DEVICE

(71) Applicant: Carebay Europe Ltd, Sliema (MT)

(72) Inventor: Stephan Olson, Danderyd (SE)

(73) Assignee: Carebay Europe Ltd, Sliema (MT)

( * ) Notice: Subject to any disclaimer, the term of this patent is extended or adjusted under 35 U.S.C. 154(b) by 293 days.

(21) Appl. No.: 15/028,431

(22) PCT Filed: Oct. 8, 2014

(86) PCT No.: PCT/EP2014/071519
§ 371 (c)(1),
(2) Date: Apr. 10, 2016

(87) PCT Pub. No.: WO2015/052224
PCT Pub. Date: Apr. 16, 2015

(65) Prior Publication Data
US 2016/0250418 A1    Sep. 1, 2016

(30) Foreign Application Priority Data

Oct. 10, 2013  (SE) ..................................... 1351202

(51) Int. Cl.
*A61M 5/315* (2006.01)
*A61M 5/20* (2006.01)
*A61M 11/08* (2006.01)
*A61M 11/00* (2006.01)
*A61M 15/00* (2006.01)
*A61M 5/24* (2006.01)
*A61M 5/32* (2006.01)

(52) U.S. Cl.
CPC ...... *A61M 5/31596* (2013.01); *A61M 5/2033* (2013.01); *A61M 5/2066* (2013.01);
(Continued)

(58) Field of Classification Search
CPC ............ A61M 5/31596; A61M 11/007; A61M 15/0003; A61M 5/2033; A61M 5/2066;
(Continued)

(56) References Cited

U.S. PATENT DOCUMENTS 4,202,314 A * 5/1980 Smirnov ............... A61M 5/284
604/138

FOREIGN PATENT DOCUMENTS

FR       2741810 A1    6/1997
GB       2447787 A     9/2008
(Continued)

OTHER PUBLICATIONS

FR 2741810, Dreystadt, date: Jun. 6, 1997.*
EPO, Int'l Search Report in PCT/EP2014/071519, dated Dec. 23, 2014.

Primary Examiner — Manuel Mendez
(74) Attorney, Agent, or Firm — Piedmont Intellectual Property

(57) ABSTRACT

A medicament delivery device includes a housing, a container holder for a medicament container, a first energy-accumulating member for powering a dispensing of a medicament from the medicament container, a releasable first locking arrangement for locking the first energy-accumulating member in a first energy-storing position, a second energy-accumulating member for powering a mixing of the medicament in the medicament container, and a releasable second locking arrangement for locking the second energy-accumulating member in a second energy-storing position. The second locking arrangement in a first state prevents the first locking arrangement from being released, and in a second state permits the first locking arrangement to be released.

21 Claims, 4 Drawing Sheets

(52) U.S. Cl.
CPC ...... *A61M 5/3157* (2013.01); *A61M 5/31515* (2013.01); *A61M 5/31585* (2013.01); *A61M 11/007* (2014.02); *A61M 11/08* (2013.01); *A61M 15/0003* (2014.02); *A61M 5/31583* (2013.01); *A61M 2005/2073* (2013.01); *A61M 2005/2451* (2013.01); *A61M 2005/3267* (2013.01); *A61M 2202/04* (2013.01); *A61M 2205/581* (2013.01); *A61M 2205/582* (2013.01); *A61M 2205/8281* (2013.01)

(58) Field of Classification Search
CPC ............ A61M 5/31515; A61M 5/3157; A61M 5/31585; A61M 11/08; A61M 5/31583; A61M 2005/2073; A61M 2005/2451; A61M 2005/3267; A61M 2205/8281; A61M 2205/582; A61M 2205/581; A61M 2202/04
USPC ........................................................ 604/82
See application file for complete search history.

(56) References Cited

FOREIGN PATENT DOCUMENTS

| | | |
|---|---|---|
| WO | 2012/173553 A1 | 12/2012 |
| WO | 2015/052221 A1 | 4/2015 |

\* cited by examiner

MEDICAMENT DELIVERY DEVICE

TECHNICAL FIELD

Embodiments disclosed herein relate to medicament delivery devices for the administering of medicaments.

BACKGROUND

The present invention relates to medicament delivery devices such as automatic injection devices for injecting liquid medicament with a needle in a patient and nebulisers for administering a medicament in the form of a mist to be inhaled into the lungs of a patient.

Auto-injectors, or pen-injectors have been on the market for many years. During recent years some medicaments have been developed to be injected by patients themselves. Therefore, depending on the intended use and type of medicament, there have also been developed injection devices having a varying degree of automatic functions to facilitate the injection of medicaments in a reliable and safe way for patients and even for trained personnel; e.g. physicians and nurses.

WO 2012/173553 discloses an injection device comprising a housing and a container holder arranged within the housing. The container holder is configured for accommodating a medicament container having a needle attached to one end thereof and a stopper sealingly and slidable arranged inside the medicament container at the other end thereof. A plunger rod is arranged with a proximal end thereof contactable with the stopper. A first and a second energy accumulating member is arranged in the interior of the housing of the injection device and adapted to accumulate and store energy. A plunger drive means is slidably arranged in relation to the plunger rod, is rotationally locked to the plunger rod, and is rotatable in relation to the housing. The plunger drive means is operationally associated with the first energy accumulating member. A container driver is arranged for being connectable to the container holder and is threadedly connected to the plunger rod. The container driver is operationally associated with the second energy accumulating member such that due to an output axial force from the second energy accumulating member, the container holder and the plunger rod are axially moveable in relation to the housing a predetermined distance towards the proximal end of the injection device from an initial locked position to a second position whereby a needle penetration is performed. The plunger drive means is locked from being rotated by the container driver. The plunger drive means is released such that due to an output torque from the first energy accumulating member the plunger drive means is allowed to be rotated and the plunger rod is urged towards the proximal end of the injection device whereby an injection is performed.

Some medicaments administered via medicament delivery devices comprise two medicament components, which require mixing before being administered via a relevant medicament delivery device such as an injection device or a nebuliser.

In such medicament delivery devices there is a requirement that the medicament components are mixed before the medicament is administered to a patient.

SUMMARY

It is an object of embodiments to ensure in a medicament delivery device that two individual procedures are performed in a specific order.

According to an aspect, this is achieved by a medicament delivery device comprising: a housing, a container holder for a medicament container arranged in the housing, a first energy accumulating member for powering a dispensing of a medicament from the medicament container, and a releasable first locking arrangement for locking the first energy accumulating member in a first energy storing position. The medicament delivery device further comprises: a second energy accumulating member for powering a mixing of a medicament in the medicament container, and a releasable second locking arrangement for locking the second energy accumulating member in a second energy storing position. The second locking arrangement in a first state prevents the first locking arrangement from being released. The second locking arrangement in a second state permits the first locking arrangement to be released.

Since the second locking arrangement in a first state prevents the first locking arrangement from being released, the second locking arrangement has to be set in its second state before the first locking arrangement is releasable. Thus, the first locking arrangement locks the first energy accumulating member in the first energy storing position until the second locking arrangement has been set in its second state. As a result, the above mentioned object is achieved.

The medicament delivery devices may be for instance be an injection device for injecting medicament in fluid form, or a nebuliser for administering a medicament in the form of a mist to be inhaled into the lungs. The medicament is at least partially administered powered by the first energy accumulating member displacing the plunger. The medicament delivery member may comprise a needle as used in an injection device, or a nozzle as used in a nebuliser.

According to embodiments, the first locking arrangement may comprise a first release mechanism movable between a first locking position locking the first energy accumulating member in the first energy storing position and a first release position releasing the first energy accumulating member from the first energy storing position. The second locking arrangement may comprise a second release mechanism movable between a second locking position locking the second energy accumulating member in the second energy storing position and a second release position releasing the second energy accumulating member from the second energy storing position. In the first state, the second release mechanism in the second locking position may prevent the first release mechanism from being moved to the first release position. In the second state, the second release mechanism in the second release position may permit the first release mechanism to be moved to the first release position. In this manner the second release mechanism as such may prevent the first locking arrangement from being released.

According to embodiments, the second release mechanism may be arranged in a blocking abutment with the first release mechanism when the second release mechanism is in the second locking position and the first release mechanism is in the first locking position. The second release mechanism may be moved out of the blocking abutment with the first release mechanism when the second release mechanism is moved to the second release position. In this manner a physical contact between the first and second release mechanisms prevents the first locking arrangement from being released.

According to embodiments, the first release mechanism may be connected to the housing such that in the first locking position the first locking arrangement is secured to the housing to maintain the first energy accumulating member in the first energy storing position. The second release mechanism may be connected to the housing such that in the second locking position the second locking arrangement is secured to the housing to maintain the second energy accumulating member in the second energy storing position.

According to embodiments, the first release mechanism may be manually movable between the first locking position and the first release position. The second release mechanism may be manually movable between the second locking position and the second release position. In this manner a user of the medicament delivery device may manually controlled the first and second release mechanisms.

According to embodiments, the housing may have a longitudinal axis extending between, and along, a proximal end portion and a distal end portion of the housing. The container holder may be arranged in the housing at the proximal end portion. The medicament delivery device may comprise a plunger. The plunger may be axially movable and may be adapted to be displaced along the longitudinal axis into the container holder. The first energy accumulating member may be adapted to displace the plunger along the longitudinal axis towards the proximal end portion for the said powering a dispensing of a medicament when released from the first energy storing position. The container holder may be adapted to accommodate a medicament container adapted for connection of a medicament delivery member at a first end portion of the medicament container and may comprise a first piston sealingly and slidably arranged inside an opposite end portion of the medicament container and a second piston slidably arranged inside an intermediate portion of the medicament container. The plunger may comprise an outer plunger rod and an inner plunger rod arranged at least partially inside the outer plunger rod. The second energy accumulating member may be arranged to actuate the inner plunger rod for the said powering a mixing of a medicament when released from the second energy storing position. In this manner a mixing of two medicament components in a medicament container may be achieved by a plunger comprising an outer and an inner plunger rod. The plunger as such may be may utilized for dispensing the mixed medicament from the medicament container.

According to embodiments, the second energy accumulating member may be arranged inside the outer plunger rod and may comprise a compression spring extending along the longitudinal axis, which compression spring in the second energy storing position may be subjected to an axial compression. The second locking arrangement may comprise a compression rod extending along the longitudinal axis. When the second locking arrangement is in the second locking position the compression rod may be engaged with the compression spring and with the housing at the distal end portion to achieve the axial compression. In this manner a compact second locking arrangement for holding the compression spring in its energy storing position may be achieved.

According to embodiments, the inner plunger rod may be adapted to engage with the outer plunger rod when the inner plunger rod is positioned in an end position towards the proximal end portion. In this manner it may be ensured that the inner plunger rod remains in a position towards the proximal end portion when the entire plunger is to be displaced towards the proximal end portion to administer a medicament from the medicament container in the container holder.

According to embodiments, the inner plunger rod may comprise at least one resilient projection adapted to engage with a recess in the outer plunger rod when the inner plunger rod is positioned in the end position towards the proximal end portion. In this manner the inner plunger rod may engage with the outer plunger rod.

According to embodiments, the outer plunger rod may be provided with a series of elevations and/or depressions. The resilient projection may be adapted to run in abutment along the series of elevations and/or depressions when the inner plunger rod is moved towards the end position towards the proximal end portion to produce an audible and/or tactile feedback to a user of the medicament delivery device. In this manner a user may be made aware when a medicament mixing has been completed in the medicament delivery device. Accordingly, when the audible or tactile feedback has ended, the user will know that the medicament is ready to be administered.

According to embodiments, the medicament delivery device may comprise a fixed member arranged inside the housing. The fixed member may be provided with a threaded inner surface. The outer plunger rod may comprise a threaded outer surface. The threaded inner surface of the fixed member may engage with the threaded outer surface of the outer plunger rod. The first energy accumulating member may comprise a torsion spring for transferring stored energy into a rotational movement for the displacing of the plunger along the longitudinal axis towards the proximal end portion. A first end of the torsion spring may be connected to the housing and a second end of the torsion spring may be connected to the outer plunger rod. The first locking arrangement may comprise a first locking member connected with the second end of the torsion spring, the first release mechanism engaging with the first locking member in the first locking position. In this manner a sufficient force for administering a medicament may be provided within a comparatively small space. Further, the torque from the torsion spring may be transferred to the plunger rod. Moreover, energy may be stored in the torsion spring until the second end of the torsion spring is released from engagement with the housing.

According to embodiments, the outer plunger rod may be engaged with the second end of the torsion spring via a drive member, the outer plunger rod being slidably connected with the drive member for sliding movement of the outer plunger rod along the drive member and the longitudinal axis. The first locking member may be connected with the drive member to be rotatable together with the second end of the torsion spring. In this manner the torque from the torsion spring may be transferred via the drive member to the plunger rod when the first locking member has been released. The outer plunger rod will slide along the longitudinal direction in the drive member while the drive member is rotated. The rotation of the outer plunger rod will advance the plunger towards the proximal end portion as the threaded outer surface of the outer plunger rod engages with the threaded inner surface of the fixed member.

According to embodiments, the first locking member may be provided with a recess and the first release mechanism may be provided with a protrusion. The protrusion may engage with the recess when the first locking member is in the first locking position.

According to embodiments, upon rotation of the first locking member, the protrusion and the recess may produce an audible and/or tactile feedback to a user of the medicament delivery device. In this manner a user may be made aware when the administering of a medicament has been completed. Accordingly, when the audible or tactile feedback has ended, the user will know that the medicament has been completed.

Further features and advantages will become apparent when studying the appended claims and the following detailed description.

BRIEF DESCRIPTION OF THE DRAWINGS

Various aspects of embodiments, including their particular features and advantages, will be readily understood from the example embodiments discussed in the following detailed description and the accompanying drawings, in which.

DETAILED DESCRIPTION

Aspects of example embodiments will now be described more fully. Like numbers refer to like elements throughout. Well-known functions or constructions will not necessarily be described in detail for brevity and/or clarity.

Figure 1:
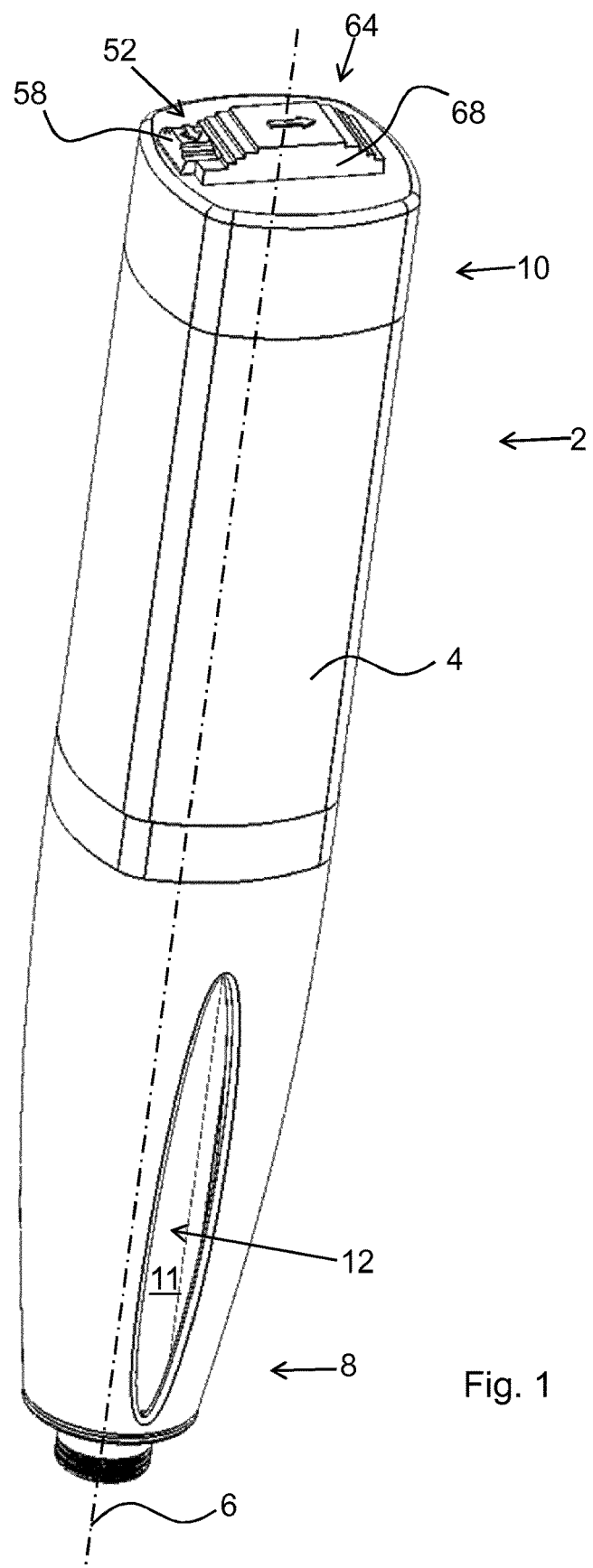
FIG. 1 illustrates a medicament delivery device according to embodiments.

FIG. 1 illustrates a medicament delivery device 2 according to embodiments. The medicament delivery device 2 comprises a housing 4. The housing 4 has a longitudinal axis 6 extending between, and along, a proximal end portion 8 and a distal end portion 10 of the housing 4. A container holder for a medicament container is arranged in the housing 4 at the proximal end portion 8. The container holder is adapted to accommodate a medicament container 11 adapted for connection of a medicament delivery member. The medicament container 11 is visible through a window 12 in the housing 4.

Figure 2:
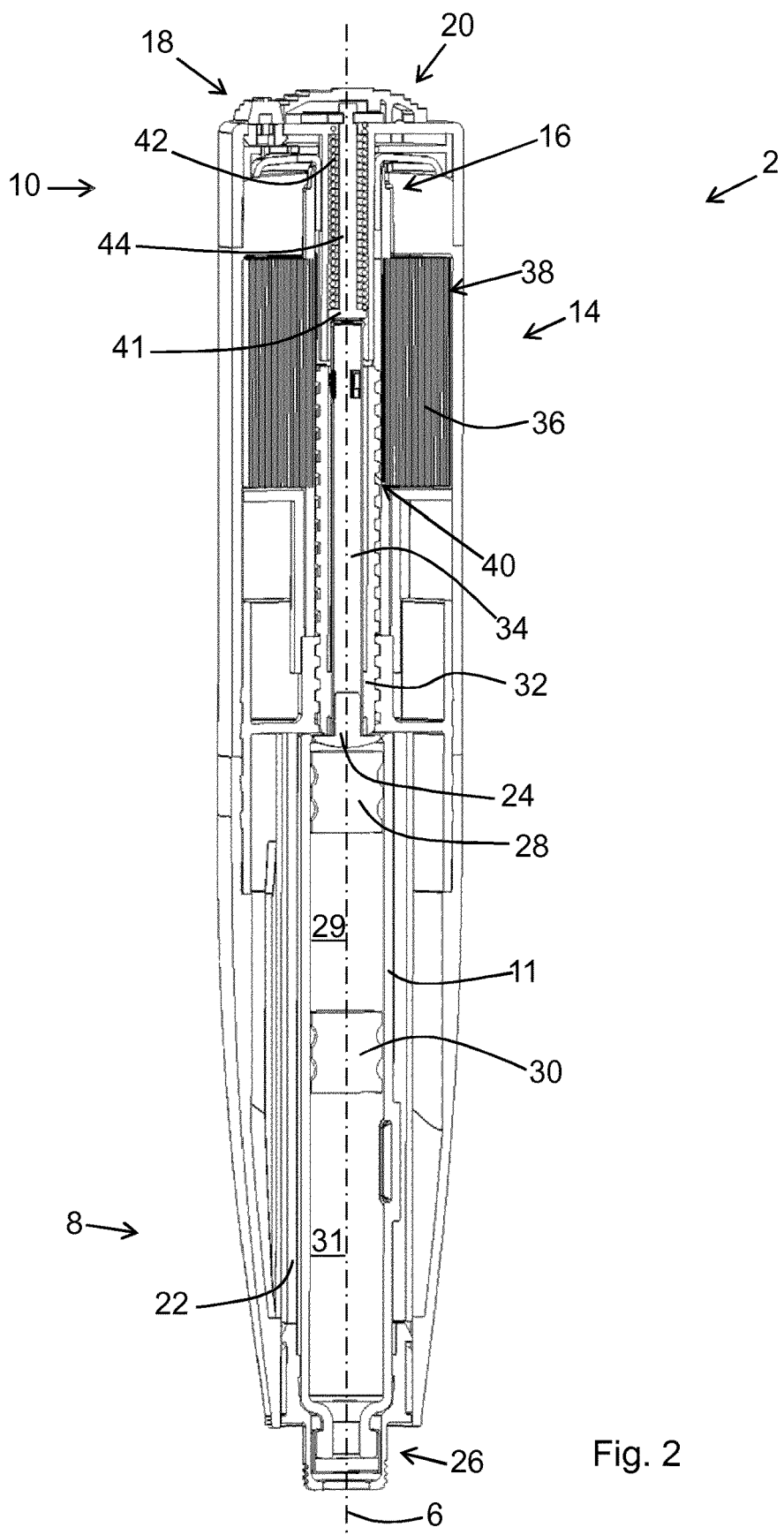
FIGS. 2 and 4-6 illustrate cross sections through the medicament delivery device illustrated in FIG. 1.

FIG. 2 illustrates a cross section through the medicament delivery device 2 illustrated in FIG. 1. The medicament delivery device 2 comprise a first energy accumulating member 14 for powering a dispensing of a medicament from the medicament container 11 and a second energy accumulating member 16 for powering a mixing of a medicament in the medicament container 11. The medicament delivery device 2 further comprises a releasable first locking arrangement 18 for locking the first energy accumulating member 14 in a first energy storing position and a releasable second locking arrangement 20 for locking the second energy accumulating member 16 in a second energy storing position. The second locking arrangement 20 in a first state prevents the first locking arrangement 18 from being released. The second locking arrangement 20 in a second state permits the first locking arrangement 18 to be released.

Figure 4:
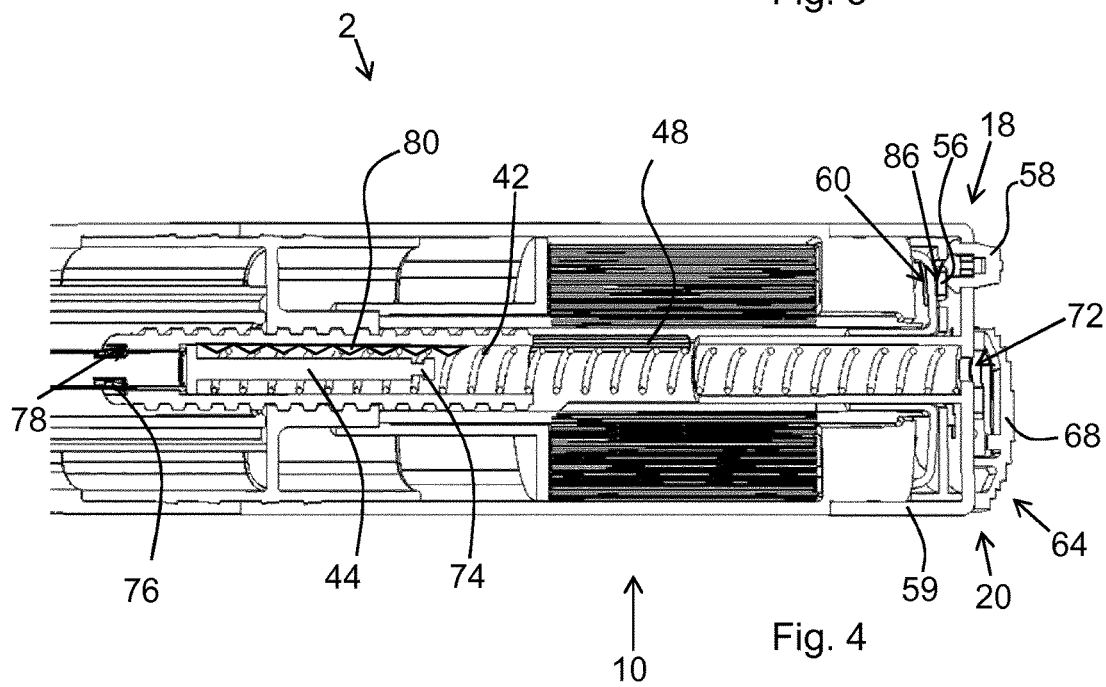
Figure 5:
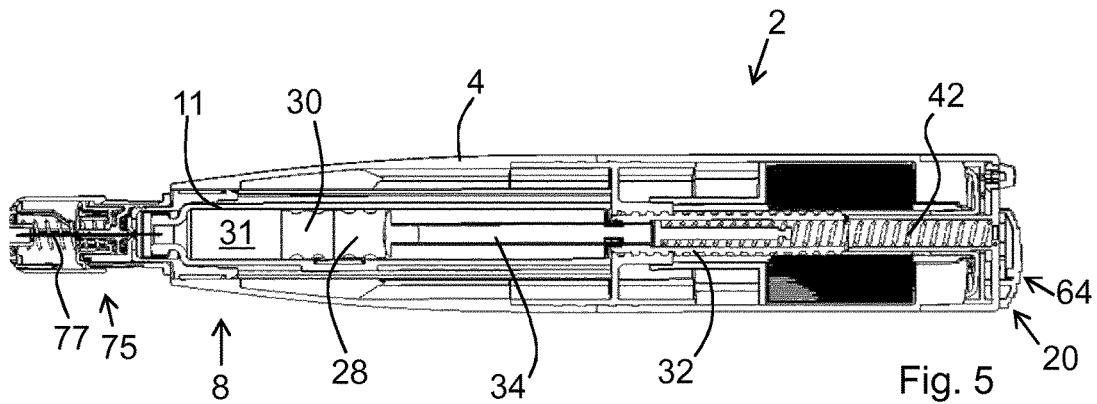

In FIGS. 1 and 2 the second locking arrangement 20 is illustrated in its first state and in FIGS. 4 and 5 the second locking arrangement 20 is illustrated in its second state.

The container holder 22 is arranged in the housing 4 at the proximal end portion 8. An axially movable plunger 24 is adapted to be displaced along the longitudinal axis 6 into the container holder 22. When the first energy accumulating member 14 is released from the first energy storing position, it powers a displacing of the plunger 24 along the longitudinal axis 6 towards the proximal end portion 8 to dispense a medicament from the medicament container 11.

The medicament container 11 is adapted for connection of a medicament delivery member at a first end portion 26 of the medicament container 11. The medicament container 11 comprises a first piston 28 sealingly and slidably arranged inside an opposite end portion of the medicament container 11 and a second piston 30 slidably arranged inside an intermediate portion of the medicament container 11. Such a medicament container 11 is adapted to contain two medicament components, one of which is stored in a first space 29 between the first piston 28 and the second piston 30. The other medicament component is stored in a second space 31 between the first end portion of the medicament container 11 and the second piston 30. For instance, the first medicament component may be a liquid component and the second medicament components may be a liquid component or a powder. The two medicament components require mixing before being administered to a patient.

The plunger 24 comprises an outer plunger rod 32 and an inner plunger rod 34 arranged at least partially inside the outer plunger rod 32. When the second energy accumulating member 16 is released from the second energy storing position, it powers an actuation of the inner plunger rod 34 for mixing two medicament components of a medicament in the medicament container 11. When released, the second energy accumulating member 16 moves the inner plunger rod 34 along the longitudinal axis 6 into the medicament container 11.

It is to be noted that, in sequence, the second energy accumulating member 16 is to be released before the first energy accumulating member 14 is released. This is ensured by the second locking arrangement 20 in the first state preventing the first locking arrangement 18 from being released.

The first energy accumulating member 14 comprises a torsion spring 36 for transferring stored energy into a rotational movement. A first end 38 of the torsion spring 36 is connected to the housing 4 and a second end 40 of the torsion spring 36 is connected to the outer plunger rod 32. The rotational movement will displace the plunger 24 along the longitudinal axis 6 towards the proximal end portion 8, as will be discussed below in connection with FIG. 6.

According to embodiments, the second energy accumulating member 16 is arranged inside the outer plunger rod 32 and comprises a compression spring 42 extending along the longitudinal axis 6. The compression spring 42 may be a spiral spring. The compression spring 42, as illustrated in FIG. 2, in the second energy storing position is subjected to an axial compression. The second locking arrangement 20 comprises a compression rod 44 extending along the longitudinal axis 6. The compression spring 42 extends about the compression rod 44. When the second locking arrangement 20 is in the second locking position, the compression rod 44 is engaged with the compression spring 42 and with the housing 4 at the distal end portion 10 to achieve the axial compression. The compression spring 42 is compressed between a wide portion 41 of the compression rod 44 and the housing 4.

Figure 3:
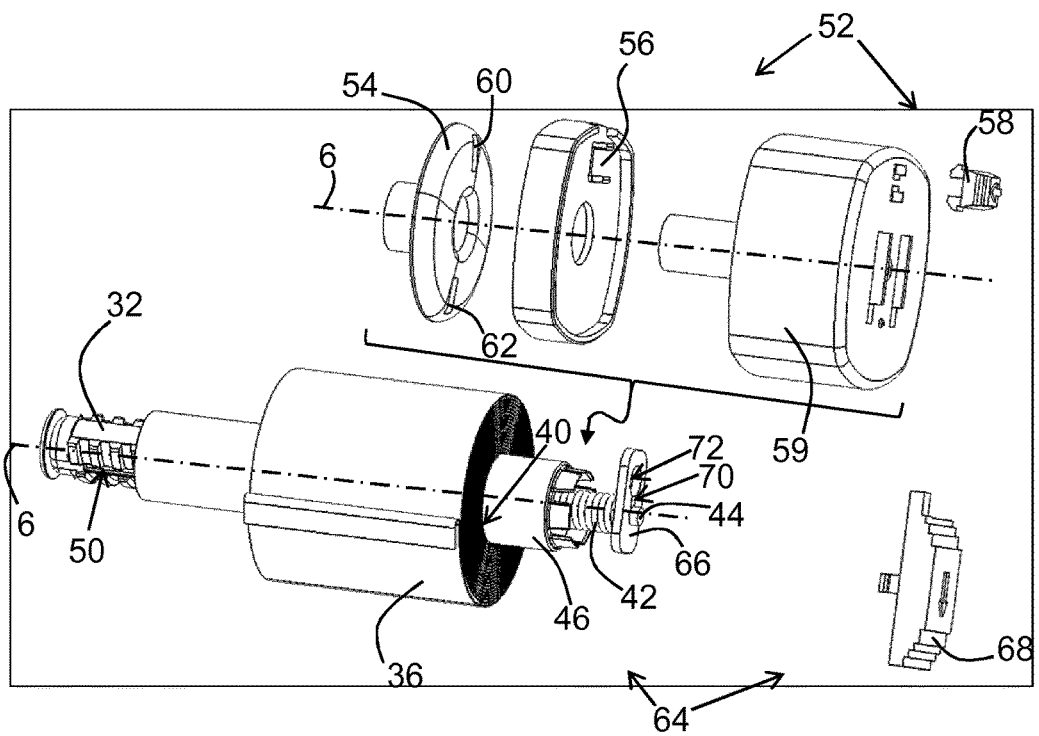
FIG. 3 illustrates an exploded view of selected components of the medicament delivery device of FIG. 1.

FIG. 3 illustrates an exploded view of selected components of the medicament delivery device 2 of FIGS. 1 and 2. The outer plunger rod 32 is engaged with the second end 40 of the torsion spring 36 via a drive member 46. The outer plunger rod 32 is slidably connected with the drive member 46 for sliding movement of the outer plunger rod 32 along the drive member 46 and the longitudinal axis 6. Such a slidable connection may for instance be achieved by an inner side of the drive member 46 being provided with at least one ridge 48, see FIG. 4, extending along the longitudinal axis 6 and an outer side of the outer plunger rod 32 being provided with at least one ridge recess 50 extending along the longitudinal axis 6. The at least one ridge 48 fits slidably in the at least one ridge recess 50.

The first locking arrangement 18 comprises a first release mechanism 52. The first release mechanism 52 is movable between a first locking position locking the first energy accumulating member 14 in the first energy storing position and a first release position releasing the first energy accumulating member 14 from the first energy storing position.

The first locking arrangement 18 comprises a first locking member 54 connected with the second end 40 of the torsion spring 36. The first locking member 54 is connected with the drive member 46 and is rotatable together with the second end 40 of the torsion spring and the drive member 46.

The first release mechanism 52 engages with the first locking member 54 in the first locking position. The first locking member 54 is provided with a recess 60 and the first release mechanism may be provided with a protrusion. The protrusion is arranged on a non-visible side of a resilient member 56 in FIG. 3. The protrusion engages with the recess 60 when the first locking member 54 is in the first locking position. The first release mechanism 52 comprises the resilient member 56 and a first slidable button 58. The first slidable button 58 is slidably connected to an outer side of an end section 59 of the housing of the medicament delivery device. Portions of the first slidable button 58 extend through slots in the end section 59 into the housing. In the first locking position, the first slidable button 58 abuts against the resilient member 56 to maintain the engagement between the protrusion and the recess 60. Thus, the first release mechanism 52 is connected to the housing such that in the first locking position the first locking arrangement 18 is secured to the housing to maintain the torsion spring 36 in the first energy storing position. See also the cross section of FIG. 4, wherein it is shown how the first slidable button 58 abuts against the resilient member 56 to maintain the engagement between the protrusion 86 and the recess 60.

In the first release position the first slidable button 58 has been slid aside by a user to permit the torque from the torsion spring 36 to overcome the engagement between the protrusion and the recess 60. On its own, the resilient member 56, no longer supported by the first slidable button 58, is not strong enough to maintain the engagement between the protrusion and the first recess 60. Thus, the resilient member 56 will bend in a direction away from the first locking member 54 due to the torque from the torsion spring 36.

Upon rotation of the first locking member 54, the protrusion and the recess 60 may produce an audible and/or tactile feedback to a user of the medicament delivery device. During rotation of the drive member 46 and the first locking member 54, the resilient member 56 biases the protrusion towards the first locking member 54. Thus, the protrusion enters and exits the recess 60 and any further recess 62 during each turn of the first locking member 54, producing the audible and/or tactile feedback.

The second locking arrangement 20 comprises a second release mechanism 64. The second release mechanism 64 is movable between a second locking position locking the second energy accumulating member 16 in the second energy storing position and a second release position releasing the second energy accumulating member 16 from the second energy storing position.

In an assembled state, the compression spring 42 extends partially through the end section 59 and the compression rod 44 extends through the end section 59. The second release mechanism 64 comprises a locking disc 66 arranged to engage with the compression rod 40. The locking disc 66 abuts slidably against the end section 59. A second slidable button 68 engages with the locking disc 66. The second slidable button 68 is slidable along an outer side of the end section 59. Portions of the second slidable button 68 extend through slots of the end section 59 to retain the second slidable button 68 against the end section 59. In the second locking position, the locking disc 66 engages with the compression rod 44. A narrow portion of the compression rod 44 fits in a narrow aperture portion 70 of the locking disc 66. Thus, the second release mechanism 64 is connected to the housing such that in the second locking position the second locking arrangement 20 is secured to the housing to maintain the compression spring 42 in the second energy storing position. To shift the second release mechanism 64 into the second release position, a user slides the second slidable button 68 and the locking disc 66 along the end section 59 such that a wide aperture portion 72 of the locking disc 66 is aligned with the compression rod 44 to release the compression rod 44.

In the first state of the second locking arrangement 20, the second release mechanism 64 in the second locking position prevents the first release mechanism 52 of the first locking arrangement 18 from being moved to the first release position. In the second state of the second locking arrangement 20, the second release mechanism 64 in the second release position permits the first release mechanism 52 to be moved to the first release position.

As may be seen in FIG. 1, the second release mechanism 64 is arranged in a blocking abutment with the first release mechanism 52 when the second release mechanism 64 is in the second locking position and the first release mechanism 52 is in the first locking position. More specifically, the second slidable button 68 of the second release mechanism 64 is arranged in a blocking abutment with the first slidable button 58 of the first release mechanism 52. As may be seen in e.g. FIG. 4, the second release mechanism 64 has been moved out of the blocking abutment with the first release mechanism 52 when the second release mechanism has been moved to the second release position. More specifically, the second slidable button 68 of the second release mechanism 64 has been moved out of the blocking abutment with the first slidable button 52.

As mentioned above, a user may slide the first and second slidable buttons 58, 68 along the end section 59. Accordingly, the first release mechanism 52 is manually movable between the first locking position and the first release position and the second release mechanism 64 is manually movable between the second locking position and the second release position.

FIG. 4 illustrates a partial cross section through a distal end portion 10 of the medicament delivery device 2 illustrated in FIGS. 1-3. The second slidable button 68 of the second release mechanism 64 has been slid along the end section 59 to release the compression rod 44. The wide aperture portion 72 of the locking disc 66 has been aligned with the compression rod 44 to release the narrow portion 74 of the compression rod 44. Thus, the second release mechanism 64 has been moved from the second locking position to the second release position releasing the compression spring 42 from its second energy storing position. Accordingly, the second locking arrangement 20 has been released and the second locking arrangement 20 is in the second state which will permit the first locking arrangement 18 to be released, see further below with reference to FIG. 6.

The inner plunger rod 34 has engaged with the outer plunger rod 32 in the illustrated position, when the inner plunger rod 34 is positioned in an end position towards the proximal end portion 8 of the housing 4. More precisely, the inner plunger rod 34 comprises at least one resilient projection 76 engaging with a recess 78 in the outer plunger rod 34.

The outer plunger rod 32, on its inside, is provided with a series of elevations and/or depressions 80. The at least one resilient projection 76 is adapted to run in abutment along the series of elevations and/or depressions 80 when the inner plunger rod 32 is moved towards the end position towards the proximal end portion 8 to produce an audible and/or tactile feedback to a user of the medicament delivery device 2.

FIG. 5 illustrates a cross section through the medicament delivery device 2 illustrated in FIGS. 1-4. Just like in FIG. 4, the second release mechanism 64 has been moved from the second locking position to the second release position releasing the compression spring 42 from its second energy storing position. The compression spring 42 has moved the inner plunger rod 34 to extend out of the outer plunger rod 32 and into the medicament container 11. The first piston 28 in the medicament container 11 has been moved towards the second piston 30 by the inner plunger rod 34. Thus, the two medicament components have been mixed in the second space 31.

Finally, a user has connected a medicament delivery member 75 to the medicament container 11. The medicament delivery member 75 has been attached to the housing 4 and a needle 77 of the medicament delivery member 75 extends into the medicament container 11. The medicament delivery device 2 is now ready for injecting the medicament into a patient.

Figure 6:
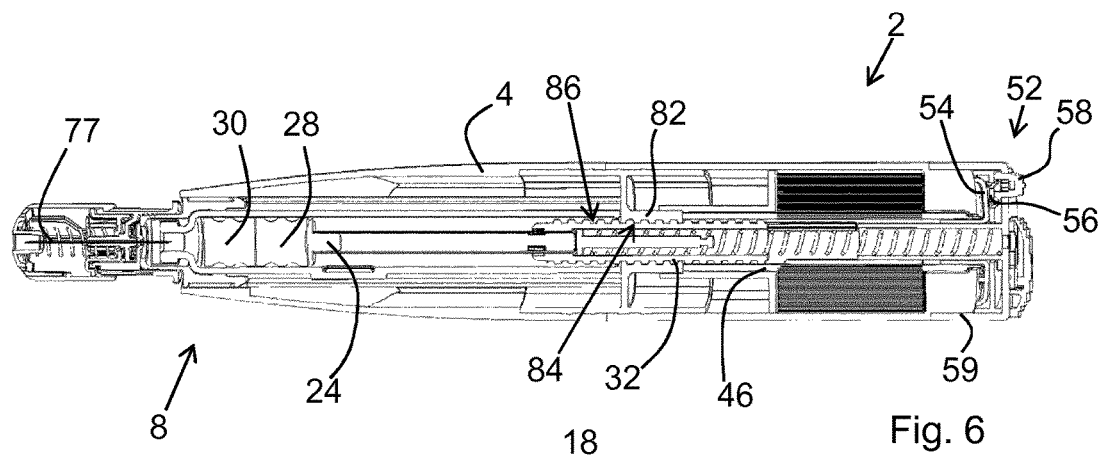

FIG. 6 illustrates a cross section through the medicament delivery device 2 of FIGS. 1-5. The medicament delivery device 2 comprises a fixed member 82 arranged inside the housing 4. The fixed member 82 is provided with a threaded inner surface 84. The outer plunger rod 32 comprise a threaded outer surface 86. The threaded inner surface 84 engages with the threaded outer surface 86.

In FIG. 6 the medicament in the medicament delivery device 2 has been administered to a patient. The needle 77 of the medicament delivery member 75 has been inserted in the patient and the first slidable button 58 of the first release mechanism 52 has been slid along the end section 59 to release the first locking member 54, i.e. the first slidable button 58 abuts no longer against the resilient member 56. Thus, the protrusion of the resilient member 56 no longer engages with the recess of the first locking member 54. Accordingly, the first release mechanism 52 has been moved from the first locking position to the first release position releasing the torsion spring 36 from its first energy storing position.

The torsion spring 36 has rotated the drive member 46 and the outer plunger rod 32. Due to the engagement between the threaded outer surface 86 of the outer plunger rod 32 and the threaded inner surface 84 of the fixed member 82, the plunger 24 has been advanced towards the proximal end portion 8, moving the first and second pistons 28, 30 towards the proximal end portion 8, to inject the medicament through the needle 77 into the patient.

Figure 7:
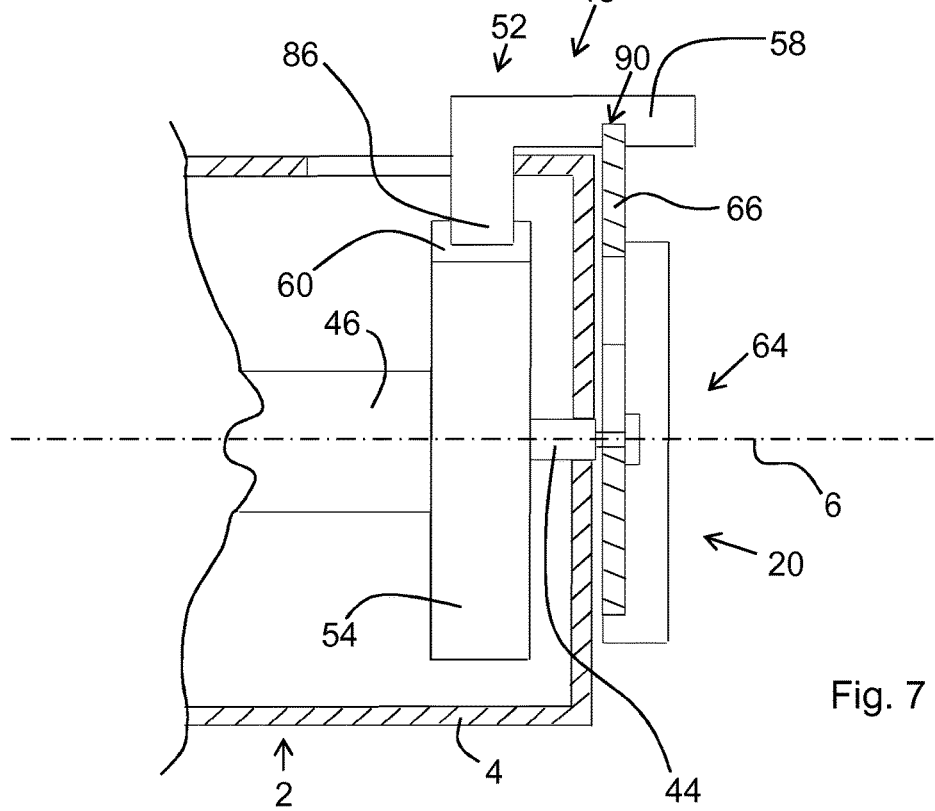
FIG. 7 illustrates a partial cross section through alternative embodiments of first and second locking arrangements of a medicament delivery device.

FIG. 7 illustrates a partial cross section through alternative embodiments of first and second locking arrangements 18, 20 of a medicament delivery device 2. The second locking arrangement 20 may be of a similar kind as the second locking arrangement 20 discussed in connection with the embodiments of FIGS. 1-6, wherein a second release mechanism 64 of the second locking arrangement 20 engages with a compression rod 44.

The first locking arrangement 18 comprises a first release mechanism 52. A locking member 54 of the first locking arrangement 18 is rotated together with a drive member 46. Again, the drive member 46 is rotated by a torsion spring (not shown) about a longitudinal axis 6 of the medicament delivery device 2. A recess 60 is provided in an axially extending surface of the first locking member 54. A protrusion 86 of a first slidable button 58 of the first release mechanism 52 engages with the recess 60. Thus, the first locking arrangement 18 locks the torsion spring in its first energy storing position. The first release mechanism 52 is movable between a first locking position locking the torsion spring in the first energy storing position and a first release position releasing the torsion spring from the first energy storing position.

The first slidable button 58 is connected to a housing 4 of the medicament delivery device 2 and extends beyond an axially extending surface of the housing 4. The first slidable button 58 is provided with a button recess 90. A disc 66 of the release mechanism 64 extends beyond a radially extending surface of the housing 4. The disc 66 extends into the button recess 90. Thus, the second locking arrangement 20 in a first state prevents the first locking arrangement 18 from being released.

The second release mechanism 64 is arranged in a blocking abutment with the first release mechanism 52 when the second release mechanism 64 is in the second locking position and the first release mechanism 52 is in the first locking position. More specifically, the disc 66 is arranged in a blocking abutment with the first slidable button 58 in the button recess 90.

The second release mechanism 64 is movable between a second locking position locking the second energy accumulating member in the second energy storing position and a second release position releasing the second energy accumulating member from the second energy storing position. In the second release position the disc 66 is slid out of engagement with the compression rod 44 and out of the button recess 90. When the second release mechanism 64 is in the second release position the second locking arrangement 20 is in the second state. After the disc 66 has released the compression rod 44 the first sliding button 58 is no longer engaged by the disc 66 in the button recess 90. Thus, the first sliding button 58 may be slid axially to release the torsion spring.

In FIG. 7 the first release mechanism 52 is illustrated in the first locking position and the second release mechanism 64 is illustrated in the second locking position.

Again, in the first state of the second locking arrangement 20, the second release mechanism 64 in the second locking position prevents the first release mechanism 52 of the first locking arrangement 18 from being moved to the first release position. In the second state the second locking arrangement 20, the second release mechanism 64 in the second release position permits the first release mechanism 52 to be moved to the first release position. The second locking arrangement 20 in a second state permits the first locking arrangement 18 to be released.

This invention should not be construed as limited to the embodiments set forth herein. A person skilled in the art will realize that different features of the described embodiments may be combined to create embodiments other than those described herein, without departing from the scope of the present invention, as defined by the appended claims. It is also understood by those skilled in the art that the medicament delivery device may be provided with further automated features such as an automatic penetration of the needle of the medicament delivery member and automatic protection of the needle after injection has been performed.

Embodiments implemented in a nebuliser, wherein the mixing of two medicament components is required before being administered, via a medicament delivery member comprising a nozzle, as a mist to be inhaled by a patient, are equally foreseen by the skilled person. Although the invention has been described with reference to example embodiments, many different alterations, modifications and the like will become apparent for those skilled in the art. The second energy accumulating member may for instance comprise a torsion spring, which torsion spring in the energy storing position is subjected to torsional loading.

Therefore, it is to be understood that the foregoing is illustrative of various example embodiments and that the invention is defined only the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A medicament delivery device, comprising:

a housing;

a container holder that is configured for a medicament container and that is arranged in the housing;

a first energy-accumulating member for powering dispensing of a medicament from the medicament container;

a releasable first locking arrangement for locking the first energy-accumulating member in a first energy-storing position, wherein the releasable first locking arrangement is slidably connected to an outer side of the housing;

a second energy-accumulating member for powering mixing of the medicament; and a releasable second locking arrangement for locking the second energy-accumulating member in a second energy-storing position, wherein the second locking arrangement is slidably connected along the outer side of the housing and in a first state prevents the first locking arrangement from being released, and the second locking arrangement in a second state permits the first locking arrangement to be released.

2. The medicament delivery device of claim 1, wherein at least one of the releasable first locking arrangement and releasable second locking arrangement comprises a slidable button that is slid aside to use the device.

3. A medicament delivery device, comprising:

a housing;

a container holder that is configured for a medicament container and that is arranged in the housing;

a first energy-accumulating member for powering dispensing of a medicament from the medicament container;

a releasable first locking arrangement for locking the first energy-accumulating member in a first energy-storing position;

a second energy-accumulating member for powering mixing of the medicament; and a releasable second locking arrangement for locking the second energy-accumulating member in a second energy-storing position, wherein the second locking arrangement in a first state prevents the first locking arrangement from being released, and the second locking arrangement in a second state permits the first locking arrangement to be released;

wherein the housing has proximal and distal end portions, with a longitudinal axis extending between and along the proximal and distal end portions; the container holder is arranged in the housing at the proximal end portion; the medicament delivery device further comprises a plunger that is being axially movable along the longitudinal axis into the container holder; the first energy accumulating member is adapted to displace the plunger along the longitudinal axis toward the proximal end portion for powering dispensing of the medicament when released from the first energy-storing position; the container holder is configured to accommodate a medicament container that is adapted for connection of a medicament delivery member at a first end of the medicament container and that comprises a first piston sealingly and slidably arranged inside a second end portion of the medicament container opposite to the first end portion and a second piston slidably arranged inside an intermediate portion of the medicament container; the plunger comprises an outer plunger rod and an inner plunger rod arranged at least partially inside the outer plunger rod; and the second energy-accumulating member is arranged to actuate the inner plunger rod for powering mixing of the medicament when released from the second energy-storing position.

4. The medicament delivery device of claim 3, wherein the second energy-accumulating member is arranged inside the outer plunger rod and comprises a compression spring that extends along the longitudinal axis and that in the second energy-storing position is subjected to an axial compression; the second locking arrangement comprises a compression rod that extends along the longitudinal axis; and when the second locking arrangement is in the second locking position, the compression rod engages the compression spring and the distal end portion of the housing, thereby generating the axial compression.

5. The medicament delivery device of claim 3, wherein the inner plunger rod is adapted to engage the outer plunger rod when the inner plunger rod is positioned in an end position toward the proximal end portion.

6. The medicament delivery device of claim 5, wherein the inner plunger rod comprises at least one resilient projection adapted to engage a recess in the outer plunger rod when the inner plunger rod is positioned in the end position.

7. The medicament delivery device of claim 6, wherein the outer plunger rod includes a series of elevations and/or depressions; and the resilient projection is adapted to run in abutment along the series of elevations and/or depressions when the inner plunger rod is moved toward the end position, thereby producing an audible and/or tactile feedback to a user of the medicament delivery device.

8. A medicament delivery device, comprising:

a housing;

a container holder that is configured for a medicament container and that is arranged in the housing;

a first energy-accumulating member for powering dispensing of a medicament from the medicament container;

a releasable first locking arrangement for locking the first energy-accumulating member in a first energy-storing position;

a second energy-accumulating member for powering mixing of the medicament; and a releasable second locking arrangement for locking the second energy-accumulating member in a second energy-storing position, wherein the second locking arrangement in a first state prevents the first locking arrangement from being released, and the second locking arrangement in a second state permits the first locking arrangement to be released;

wherein the first locking arrangement comprises a first release mechanism movable between a first locking position locking the first energy-accumulating member in the first energy-storing position and a first release position releasing the first energy-accumulating member from the first energy-storing position; the second locking arrangement comprises a second release mechanism movable between a second locking position locking the second energy-accumulating member in the second energy-storing position and a second release position releasing the second energy-accumulating member from the second energy-storing position; in the first state the second release mechanism in the second locking position prevents the first release mechanism from being moved to the first release position; and in the second state the second release mechanism in the second release position permits the first release mechanism to be moved to the first release position.

9. The medicament delivery device of claim 8, wherein the first release mechanism is connected to the housing such that in the first locking position the first locking arrangement is secured to the housing to maintain the first energy-accumulating member in the first energy storing position; and the second release mechanism is connected to the housing such that in the second locking position the second locking arrangement is secured to the housing to maintain the second energy-accumulating member in the second energy storing position.

10. The medicament delivery device of claim 8, wherein the first release mechanism is manually movable between the first locking position and the first release position; and the second release mechanism is manually movable between the second locking position and the second release position.

11. The medicament delivery device of claim 8, wherein the housing has proximal and distal end portions, with a longitudinal axis extending between and along the proximal and distal end portions; the container holder is arranged in the housing at the proximal end portion; the medicament delivery device further comprises a plunger that is being axially movable along the longitudinal axis into the container holder; the first energy accumulating member is adapted to displace the plunger along the longitudinal axis toward the proximal end portion for powering dispensing of the medicament when released from the first energy-storing position; the container holder is configured to accommodate a medicament container that is adapted for connection of a medicament delivery member at a first end of the medicament container and that comprises a first piston sealingly and slidably arranged inside a second end portion of the medicament container opposite to the first end portion and a second piston slidably arranged inside an intermediate portion of the medicament container; the plunger comprises an outer plunger rod and an inner plunger rod arranged at least partially inside the outer plunger rod; and the second energy-accumulating member is arranged to actuate the inner plunger rod for powering mixing of the medicament when released from the second energy-storing position.

12. The medicament delivery device of claim 11, further comprising a fixed member arranged inside the housing and having a threaded inner surface; the outer plunger rod includes a threaded outer surface configured to engage the threaded inner surface (84) of the fixed member; the first energy-accumulating member comprises a torsion spring for transferring stored energy into a rotational movement for displacing the plunger along the longitudinal axis toward the proximal end portion; a first end of the torsion spring is connected to the housing; a second end of the torsion spring is connected to the outer plunger rod; and the first locking arrangement comprises a first locking member connected with the second end of the torsion spring, the first release mechanism engaging the first locking member in the first locking position.

13. The medicament delivery device of claim 12, wherein the outer plunger rod engages the second end of the torsion spring via a drive member, the outer plunger rod being slidably connected with the drive member for sliding movement of the outer plunger rod along the drive member and the longitudinal axis; and the first locking member is connected with the drive member to rotate together with the second end of the torsion spring.

14. The medicament delivery device of claim 12, wherein the first locking member includes a recess; the first release mechanism includes a protrusion; and the protrusion engages the recess when the first locking member is in the first locking position.

15. The medicament delivery device of claim 14, wherein upon rotation of the first locking member, the protrusion and the recess produce an audible and/or tactile feedback to a user of the medicament delivery device.

16. The medicament delivery device of claim 8, wherein the second release mechanism is arranged in a blocking abutment with the first release mechanism when the second release mechanism is in the second locking position and the first release mechanism is in the first locking position; and the second release mechanism is moved out of the blocking abutment with the first release mechanism when the second release mechanism is moved to the second release position.

17. The medicament delivery device of claim 16, wherein the first release mechanism is connected to the housing such that in the first locking position the first locking arrangement is secured to the housing to maintain the first energy-accumulating member in the first energy storing position; and the second release mechanism is connected to the housing such that in the second locking position the second locking arrangement is secured to the housing to maintain the second energy-accumulating member in the second energy storing position.

18. The medicament delivery device of claim 16, wherein the first release mechanism is manually movable between the first locking position and the first release position; and the second release mechanism is manually movable between the second locking position and the second release position.

19. The medicament delivery device of claim 16, wherein the housing has proximal and distal end portions, with a longitudinal axis extending between and along the proximal and distal end portions; the container holder is arranged in the housing at the proximal end portion; the medicament delivery device further comprises a plunger that is being axially movable along the longitudinal axis into the container holder; the first energy accumulating member is adapted to displace the plunger along the longitudinal axis toward the proximal end portion for powering dispensing of the medicament when released from the first energy-storing position; the container holder is configured to accommodate a medicament container that is adapted for connection of a medicament delivery member at a first end of the medicament container and that comprises a first piston sealingly and slidably arranged inside a second end portion of the medicament container opposite to the first end portion and a second piston slidably arranged inside an intermediate portion of the medicament container; the plunger comprises an outer plunger rod and an inner plunger rod arranged at least partially inside the outer plunger rod; and the second energy-accumulating member is arranged to actuate the inner plunger rod for powering mixing of the medicament when released from the second energy-storing position.

20. The medicament delivery device of claim 19, wherein the second energy-accumulating member is arranged inside the outer plunger rod and comprises a compression spring that extends along the longitudinal axis and that in the second energy-storing position is subjected to an axial compression; the second locking arrangement comprises a compression rod that extends along the longitudinal axis; and when the second locking arrangement is in the second locking position the compression rod engages the compression spring and the housing at the distal end portion, thereby generating the axial compression.

21. The medicament delivery device of claim 20, wherein the inner plunger rod is adapted to engage the outer plunger rod when the inner plunger rod is positioned in an end position toward the proximal end portion.

\* \* \* \* \*